United States Patent [19]

Buhler

[11] 4,185,896
[45] Jan. 29, 1980

[54] REFRACTOR CROSS-CYLINDER APPARATUS

[75] Inventor: Rato Buhler, Dudley, Mass.

[73] Assignee: American Optical Corporation, Southbridge, Mass.

[21] Appl. No.: 881,341

[22] Filed: Feb. 27, 1978

[51] Int. Cl.² ............................................. A61B 3/02
[52] U.S. Cl. ....................................... 351/29; 351/28
[58] Field of Search ................................. 351/28, 29

[56] References Cited

U.S. PATENT DOCUMENTS

| | | | |
|---|---|---|---|
| 3,498,699 | 3/1970 | Wilkinson | 351/28 X |
| 3,698,799 | 10/1972 | Pitchford | 351/28 |
| 3,860,330 | 1/1975 | Persson | 351/28 X |

FOREIGN PATENT DOCUMENTS 2555387  6/1977  Fed. Rep. of Germany ............. 351/29

Primary Examiner—Paul A. Sacher
Attorney, Agent, or Firm—Jeremiah J. Duggan; Alan H. Spencer; Stephen A. Schneeberger

[57] ABSTRACT

A pair of cylinder lenses have a combined power of zero when their cylinder axes are parallel and a small cross cylinder power when one lens is rotated until its axis is perpendicular to the cylinder axis of the other lens. Cross-cylinder lenses are used to determine the accuracy of the cylinder power and cylinder axis selected by the practitioner. By mounting one cylinder lens in a motor-driven ring-like lens mount having a member which engages another ring-like lens mount, a single motor can be used to drive both lenses; select between parallel cylinder axes and crossed cylinder axes; and rotate the crossed axis lenses as an assembly to the desired position.

8 Claims, 10 Drawing Figures

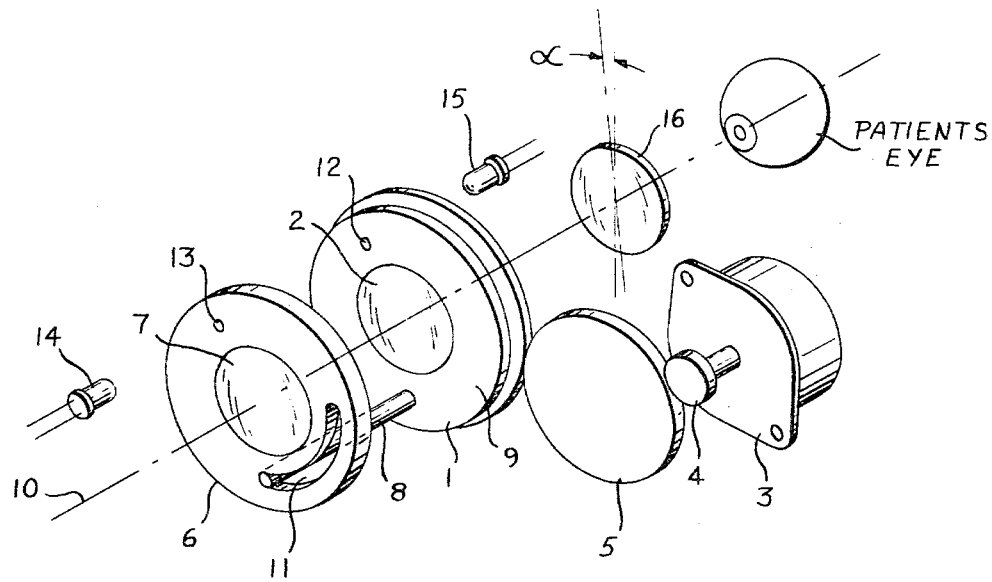
*Fig. 1*
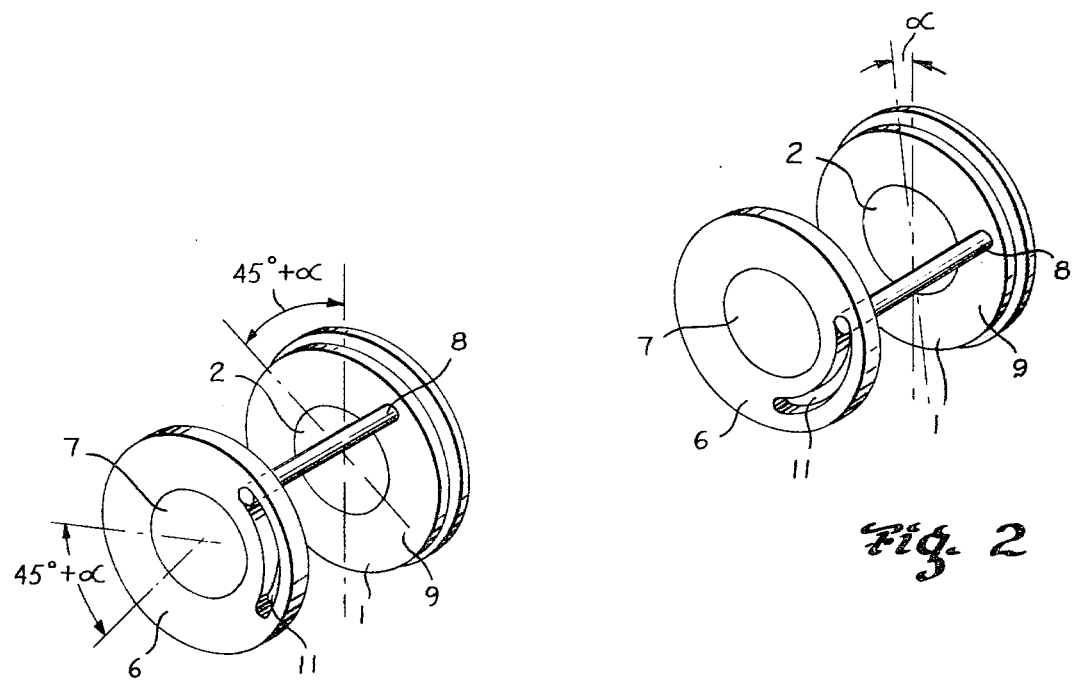
*Fig. 2*
*Fig. 3*

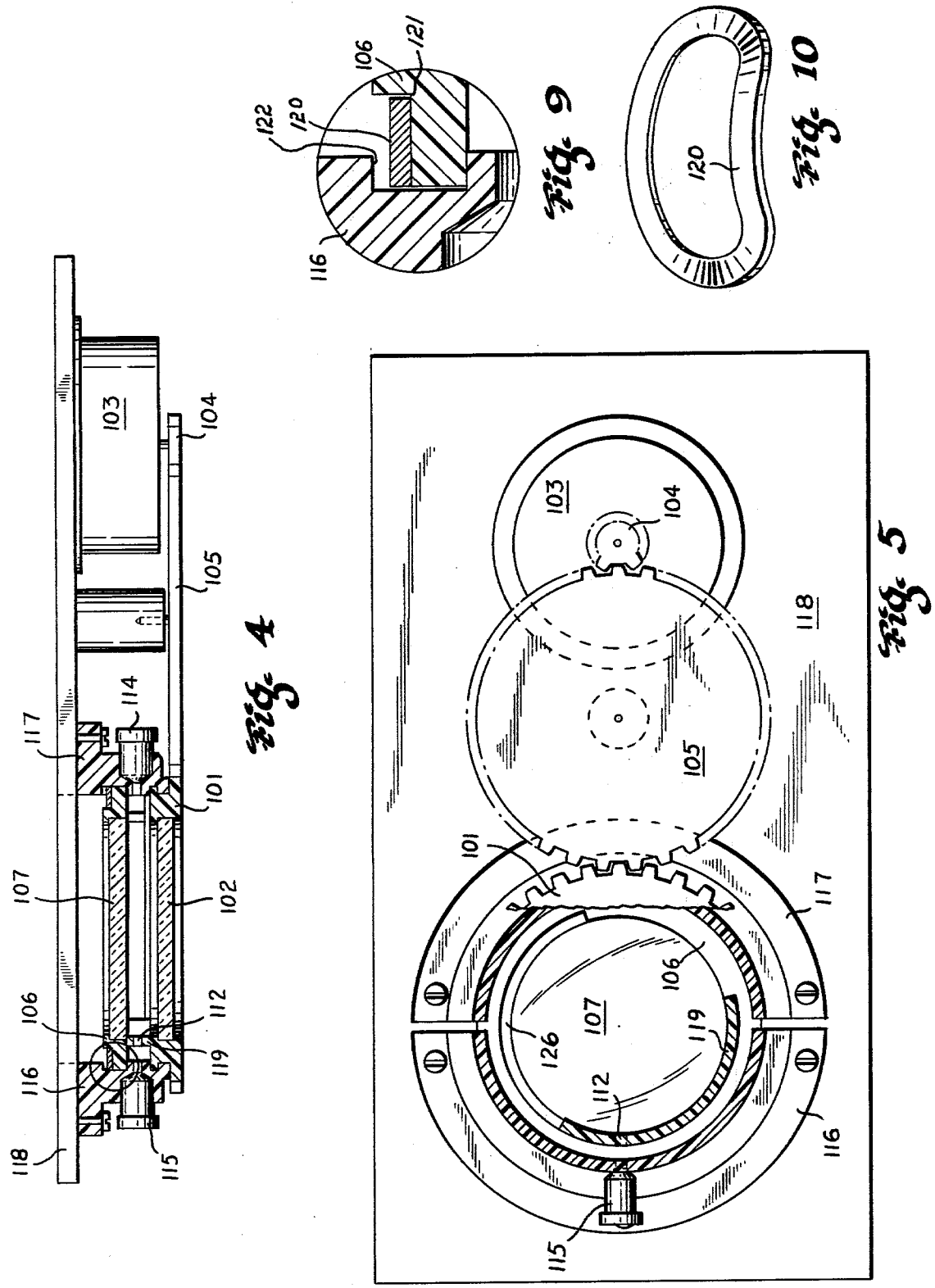

REFRACTOR CROSS-CYLINDER APPARATUS

BACKGROUND OF THE INVENTION

This invention relates to refractors and more particularly to an improved cross-cylinder mechanism.

Refractors are well-known ophthalmic instruments used for determining the proper lens values necessary to correct the defective vision of the patient. The refractor typically includes a right eye battery and a left eye battery, each enabling the practitioner to place various corrective lenses in alignment with one of the patient's eyes. Each of the batteries is alike and each includes a sphere lens assembly and a cylinder lens assembly, with each assembly including a plurality of progressively powered lenses. The practitioner may thereby select specific lenses and place them in alignment with the patient's eye to determine the proper lens values for correcting the patient's vision.

A cross-cylinder assembly is usually used for performing the Jackson cross-cylinder test to determine the accuracy of cylinder power and axis that has been selected for visual correction. The cross-cylinder assembly is usually a lens having plus and minus cylinders of equal power with their cylinder axes 90° apart. This lens is conventionally mounted in a loop which may be selectively "flipped" about a rotational axis that is perpendicular to the patient's visual (test) axis and the rotational axis is spaced midway (45°) between the plus and minus cylinder axes. When the cross-cylinder lens is flipped, the plus and minus cylinder axes exchange places. The prior art further teaches the desirability of mechanically coupling the cross-cylinder assembly to the cylinder lenses of the test battery in order that the flip axis of the cross-cylinder assembly maintains its orientation to the cylinder axis of the correcting cylinder lenses at all times. The rotational axis of the cross-cylinder assembly or flip axis, is aligned parallel to the cylinder axis of the correcting lenses when testing for the accuracy of the selected astigmatic axis. When testing for the accuracy of the power of the selected cylinder lenses, the flip axis of the cross-cylinder assembly is oriented 45° to the correcting cylinder lens axis.

U.S. Pat. No. 3,498,699, issued May 3, 1970 to Wilkinson, discloses a cross-cylinder loop assembly mechanically coupled to correcting cylinder lenses in order to maintain proper orientation of the cross-cylinder assembly and which may be moved from a position along the patient's test axis to a position away from the patient's test axis. The Cross-cylinder assembly is manually flipped along a rotational axis perpendicular to the patient's test axis to conduct the Jackson cross-cylinder tests.

U.S. Pat. No. 3,698,799 issued Oct. 17, 1972 to Pitchford, relates to a refractor having a flip cross-cylinder assembly capable of being "flipped" from a position convenient to the control used to select the correcting cylinder lens axis. Similar to Wilkinson, the device is designed to swing the cross-cylinder assembly in line with or away from the patient's test axis. Likewise, the cross-cylinder lens is flipped to conduct the tests.

U.S. Pat. No. 3,860,330, issued Jan. 14, 1975 to Staffan B. Persson, describes a mechanism for synchronizing the axial orientation of a cross-cylinder lens assembly with the cylinder axis of a correcting cylinder lens. Similar to the preceding patents described above, Persson teaches that the cross-cylinder assembly is pivotably mounted so that it can be swung from a position in alignment with the test axis to a position away from the test axis. Persson also teaches a mechanism for remotely flipping the cross-cylinder lens.

BRIEF DESCRIPTION OF THE INVENTION AND DRAWINGS

It is an object of the present invention to provide a novel cross-cylinder lens assembly.

It is a further object of the present invention to provide a cross-cylinder lens assembly which need not be removed from the test axis when the practitioner is not engaged in Jackson cross-cylinder testing.

It is a further object of the present invention to provide a cross-cylinder lens assembly which does not require flipping the cross-cylinder lens.

Still another object of the present invention is to provide a cross-cylinder lens assembly which may be conveniently operated by a single motor.

It is a still further object of the present invention to provide a cross-cylinder lens assembly which does not require mechanical connection to the cylinder lenses of a refractor in order to maintain the proper axial relationship between the cross-cylinder lens assembly and correcting cylinder lenses.

BRIEF DESCRIPTION OF THE DRAWINGS

FIG. 1 is a perspective, exploded, schematic view of the present invention;

FIG. 2 schematically shows the lenses in cross-cylinder orientation for testing for correct eye power;

FIG. 3 schematically shows the lenses in cross-cylinder eye position for testing for correct cylinder axis;

FIG. 4 is a top view, partly in section, of one embodiment of the present invention;

FIG. 5 is a front view, partly in section, of the embodiment of FIG. 4;

FIG. 9 is an enlargement of part of FIG. 4; and

FIG. 10 is a perspective view of the spring washer used in the embodiment of FIG. 4.

DETAILED DESCRIPTION OF THE INVENTION

Figure 6:
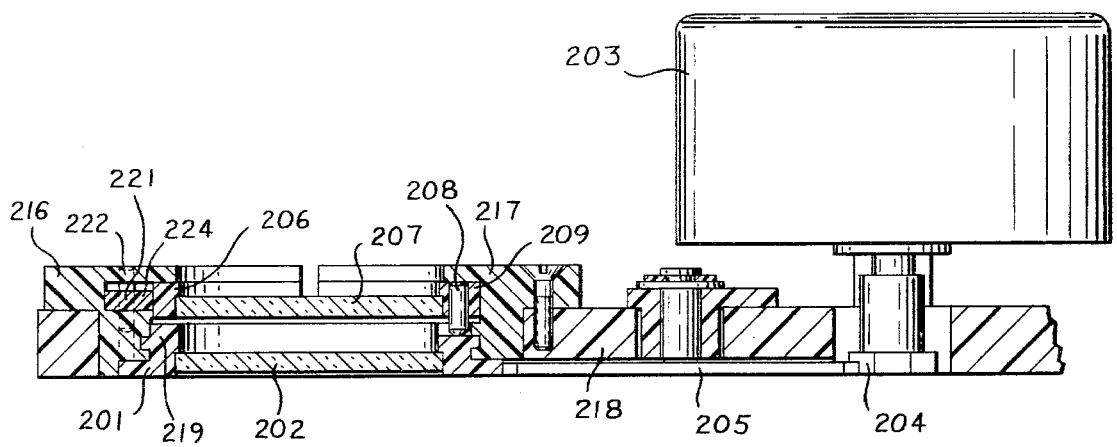
FIG. 6 is a top view, partly in section, of another embodiment of the present invention.

Referring to FIG. 1, a driving lens mount 1, carries the plus cylinder lens 2. Lens mount 1 is driven by motor 3 through drive gear 4 and idler gear 5. Driven lens mount 6 carries minus cylinder lens 7. Pin 8 extends from face 9 of driving lens mount 1 in a direction parallel to test axis 10. Driven lens mount 6 has a radially spaced recess 11 extending through a 90° arc. Driving lens mount 1 has pin hole 12 and driven lens mount 6 as pin hole 13 which permit light from LED 14 to be received by detector 15 when driving lens mount 1 and driven lens mount 6 are in the orientation shown in FIG. 1. In this orientation, the cylinder axis of the plus cylinder lens carried by driving lens mount 1 and the cylinder axis of the minus cylinder lens 7 carried by driven lens mount 6 are both vertical as indicated by the 90° meridians. This neutral position is used during the examination prior to conducting the Jackson cross-cylinder tests.

To practice the Jackson cross-cylinder tests utilizing the cross-cylinder assembly of the invention, a selected correcting cylinder lens 16 is positioned between the patient's eye and the assembly described above. The axis of correcting cylinder lens 16 is located alpha degrees from the 90° meridian. Stepping motor 3 is activated by the practitioner and rotates driving lens mount 1 clockwise 90° plus alpha. After traveling 90°, pin 8 drags driven lens mount 6 through an arc of alpha degrees. The axis of plus cylinder lens 2 is now parallel with the axis of correcting lens 16 and the axis of minus cylinder lens 7 is normal to the axis of correcting cylinder lens 16 and plus cylinder lens 2. This position is used for checking power of the correcting cylinder lens and further actuation of stepper motor 3 by the practitioner provide the equivalent of "flipping" a conventional cross-cylinder lnes by counter clockwise rotation of plus cylinder lens 2 and minus cylinder lens 7 in stages of 90° from the position shown in FIG. 2. Upon completion of the Jackson cross-cylinder test for correct lens power, the cross-cylinder assembly is returned to the position shown in FIG. 1 by clockwise rotation of driving lens mount 1 until the second signal of detector 15 receiving light through pin holes 12 and 13 from LED 14. Actuation of stepping motor 3 to rotate counter-clockwise driving lens mount 1 through an arc of 135° plus alpha provides the proper orientation for conducting the Jackson cross-cylinder test for alignment of the correcting cylinder lens axis. Further incremental counter-clockwise rotations of 90° are used in conducting the test for axis orientation. If the practitioner changes the orientation of the cylinder axis of correcting cylinder lens 16, driving lens mount 1 and driven lens mount 6 are rotated clockwise by stepping motor 3 until the second signal is received from detector 15. All changes in axis of the correcting cylinder lens are conducted with cylinder lenses 2 and 7 in the orientation shown in FIG. 1. The practitioner would then realign the crossed-cylinder lenses as shown in FIG. 3 by counter-clockwise rotation of the lens mounts through an arc of 135° plus the new alpha and the driven lens mount through an arc of 45° plus new alpha.

Since plus cylinder lens 2 and minus cylinder lens 7 have a net cylinder and/or sphere effect of zero diopter in the position shown in FIG. 1, it is unncessary that the cross-cylinder assembly be removed from the test axis at any time during the refraction period. In addition, since stepping motor 3 drives the cross-cylinder lenses to proper orientation with correcting lens 16, it is unnecessary to mechanically connect the cross-cylinder lens assembly with the battery of correcting cylinder lenses.

The Preferred Embodiments

Referring to FIG. 4, driving lens mount 101 is supported by carrier halves 116 and 117 to permit rotation of plus cylinder lens 102 carried by body 118, which is carried by driving lens mount 101. Rotation of driving lens mount 101 is provided by stepping motor 103 and drive gear 104 through idler 105. Minus cylinder lens 107 is likewise carried by driven lens mount 106 which is similarly supported by carrier halves 116 and 117. Driving lens mount 101 has a radially spaced protrusion 119 extending towards driven lens mount 106. Similarly driven lens mount 106 has a radially extending protrusion 126 extending toward driving lens mount 101. Protrusions 119 and 126 have the same radial spacing and each protrusion extends through an arc of 135°. Thus the two protrusions leave a gap having an arc of 90° therebetween as more clearly shown in FIG. 5. LED 114 and detector 115 cooperate to locate the neutral position of driving lens mount 101 by pin hole 112 in protrusion 119. The FIG. 10 shows spring washer 120 in detail. FIG. 9 is an enlargement detailing the location of spring washer 120 between face 121 of driven lens mount 106 and face 122 of lens carrier halves 116 and 117. This biasing means resists motion of driven mount 106 to prevent overrun and maintain accuracy of the critical cylinder positions. The cross-cylinder lenses function as previously described when operated by the practitioner.

Figure 7:
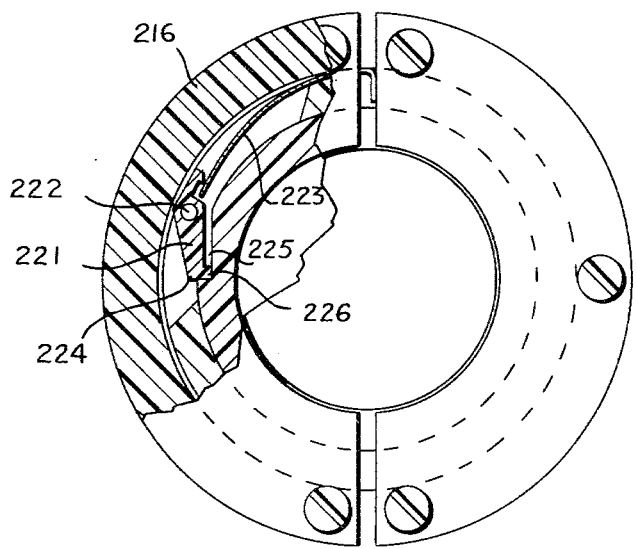
FIG. 7 is a front view, partly in section, of the cross-cylinder mounting assembly of the embodiment of FIG. 6.

FIGS. 6 and 7 illustrate an alternate preferred embodiment. As shown in FIG. 5, the structure and drive means of this embodiment is substantially the same as that of the embodiment shown in FIGS. 4 and 5. However, protrusion 219 on driving lens mount 201 extends through an arc of 270°, less the diameter of pin 208, instead of the shorter arc shown in the embodiment of FIGS. 4 and 5. Instead of an arcuate protrusion, pin 208 extends from face 209 of driven lens mount 206 in a direction toward driving lens mount 201. Pin 208 is radially spaced to engage protrusion 219 which functions in the same manner as recess 11 in FIGS. 1–3. Instead of using the light operated system to locate the neutral position of the cylinder lenses, the embodiment of FIGS. 6 and 7 utilizes a pawl and notch construction, pawl 221 is pivotably mounted by pin 222 which in turn is mounted in carrier half 216. Spring 223 biases end 224 of pawl 221 inwardly toward driven lens mount 206. Driven lens mount 206 has a peripheral recess 225 which provides a radially extending face 226. Since driving lens mount 201 and driven lens mount 206 rotate counterclockwise when the practitioner is conducting the Jackson cross-cylinder test, the pawl and recess do not interfere with such testing. However, when the practitioner desires to return to the neutral position of the cross-cylinder lenses, pawl 221 drops into the peripheral recess 225 and engages radially extending face 226 at the first opportunity. The gap in driving protrusion 219 permits an additional 90° clockwise rotation of plus cylinder lens 202 cancelling the effect of negative cylinder lens 207.

Figure 8:
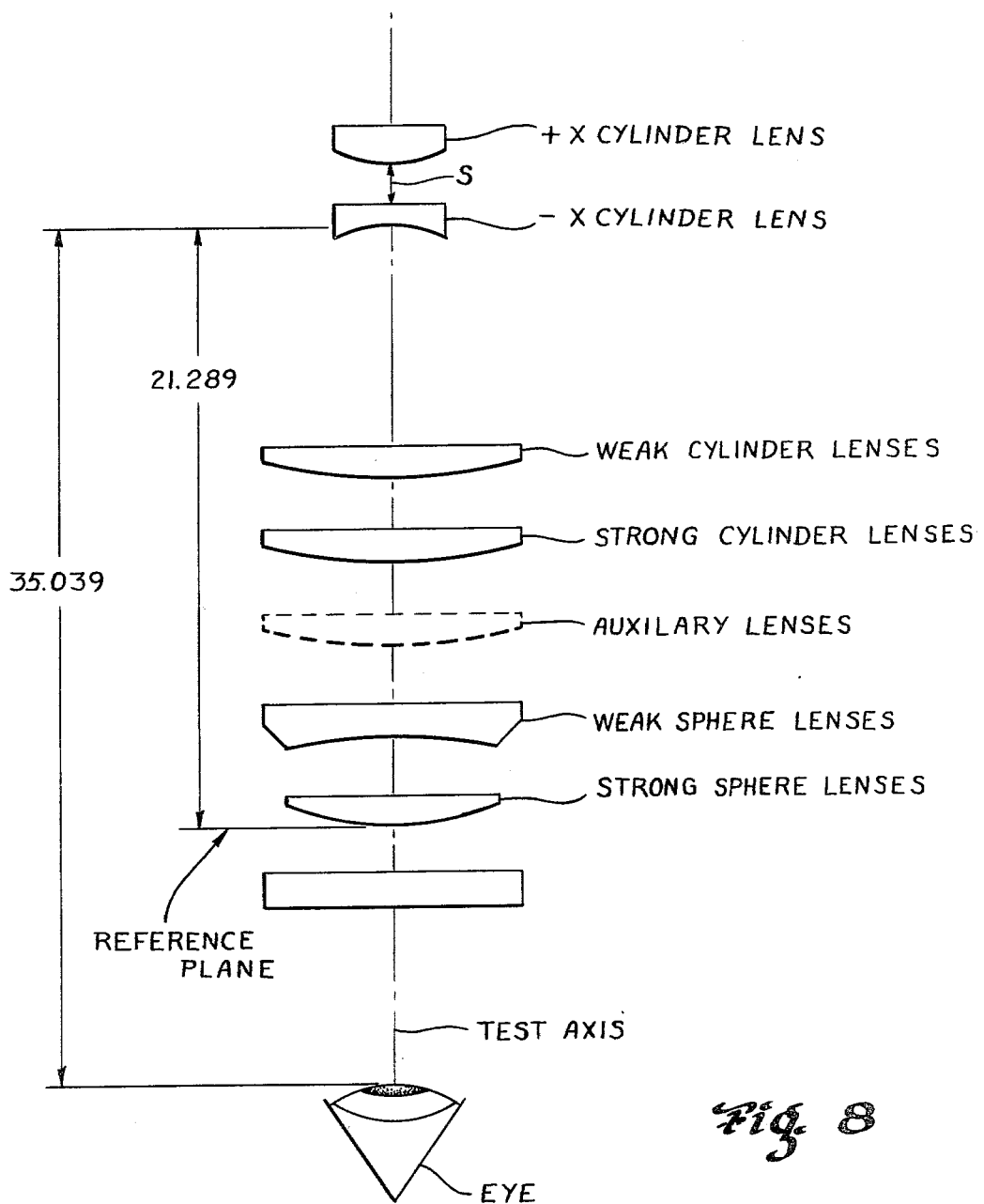
FIG. 8 is an optical diagram of a refractor lens system having an embodiment of the present invention.

Practitioners generally prefer to have cross-cylinder lenses in 0.25, 0.375, or 0.50 diopter powers. Table I provides preferred optical parameters for cross-cylinder lenses used according to the present invention which is diagramatically illustrated in FIG. 8. All distances, spacings(S) thicknesses(T) and radii(R) are in millimeters, with a minus sign (−) denoting a radius having a vertex on the eye side of the lense. The radii noted are all cylinder radii and the glass has an index of refraction of 1.523 with an Abbe number of 58.6.

TABLE

| Lens | Radius | Thickness | Spacing |
|---|---|---|---|
| 0.25 Diopter | | | |
| +cyl | ∞ | 1.6 | |
| | 2105.37 | | |
| | | | S = 3.226 |
| −cyl. | ∞ | 1.6 | |
| | −2103.13 | | |
| 0.375 Diopter | | | |
| +cyl. | ∞ | 1.6 | |
| | 1408.04 | | |
| | | | S = 3.226 |
| | ∞ | | |

TABLE-continued

| Lens | Radius | Thickness | Spacing |
|---|---|---|---|
| −cyl. | | 1.6 | |
| | −1405.80 | | |
| 0.5 Diopter | | | |
| +cyl | ∞ | 1.6 | |
| | 1059.37 | | |
| | | | S = 3.226 |
| −cyl | ∞ | 1.6 | |
| | −1057.13 | | |

What is claimed is:

1. A refractor having a body; and cylinder lenses permanently located on a testing axis with a neutral orientation or a crossed orientation, the crossed orientation being for conducting Jackson cross-cylinder tests, the cylinder lenses being of effectively equal and opposite power, which comprises,
   two ring members carried by said body and adapted to rotate about an axis coincident with the testing axis, each of said ring members being adapted to carry one of the two cylinder lenses,
   drive means for rotating one of said ring members in either direction,
   connecting means for transmitting rotational motion of said one of said ring members to the other of said ring members, said connection means including lag means permitting the other of said ring members to remain stationary during the first 90° of rotation of said one of said ring members when said one of said ring members is driven in a direction of rotation opposite to the preceding direction of rotation.

2. The refractor according to claim 1 wherein said lag means comprises two radially spaced protrusions axially extending from adjacent sides of said ring members and each protrusion having an arcuate length of 135°.

3. The refractor according to claim 1 wherein said lag means comprises a radially spaced member on said one of said ring members axially extending into an arcuate recess on said other of said ring members and said recess has an effective arcuate length of 90°.

4. The refractor according to claim 1 wherein said drive means includes a stepping motor.

5. The refractor according to claim 1 wherein the neutral position of the cylinder lenses is identified by a signal.

6. The refractor according to claim 1 wherein the signal is generated by a detector receiving light through a passage in at least one of said two rings.

7. The refractor according to claim 1 wherein said one of said ring members carries a plus cylinder lens and the other of said ring members carries a minus cylinder lens.

8. The refractor according to claim 1 wherein a biasing means frictionally retards motion of said other of said ring members.

* * * * *